(12) United States Patent
Barodka

(10) Patent No.: US 8,833,373 B2
(45) Date of Patent: Sep. 16, 2014

(54) NASALLY INSERTED AIRWAY OPENING DEVICE FOR OBSTRUCTIVE SLEEP APNEA TREATMENT

(75) Inventor: Viachaslau Mikalayevich Barodka, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 474 days.

(21) Appl. No.: 13/018,701

(22) Filed: Feb. 1, 2011

(65) Prior Publication Data
US 2012/0118297 A1 May 17, 2012

Related U.S. Application Data

(60) Provisional application No. 61/412,943, filed on Nov. 12, 2010.

(51) Int. Cl.
| | | |
|---|---|---|
| A61F 5/56 | (2006.01) | |
| A61M 29/00 | (2006.01) | |
| A61M 16/00 | (2006.01) | |

(52) U.S. Cl.
USPC ............... 128/848; 604/101.02; 128/200.26

(58) Field of Classification Search
USPC ........ 600/146; 128/846, 848, 207.13, 207.14, 128/207.15, 207.18, 200.26; 606/191, 195, 606/196, 192, 199; 604/19, 48, 93.01, 604/96.01, 101.01, 101.03, 101.02
See application file for complete search history.

(56) References Cited

U.S. PATENT DOCUMENTS

| | | | |
|---|---|---|---|
| 5,499,625 A * | 3/1996 | Frass et al. ............... | 128/207.15 |
| 6,394,093 B1 * | 5/2002 | Lethi ....................... | 128/207.18 |
| 6,536,437 B1 | 3/2003 | Dragisic | |
| 7,100,612 B2 | 9/2006 | Dunlap | |
| 8,088,101 B2 * | 1/2012 | Chang et al. ............... | 604/96.01 |
| 2010/0242967 A1 * | 9/2010 | Burbank et al. .......... | 128/207.18 |
| 2011/0109458 A1 * | 5/2011 | Shipman .................... | 340/573.1 |

OTHER PUBLICATIONS

Ahmed J., et al. "The role of the nasopharyngeal airway for obstructive sleep apnea in syndromic craniosynostosis" J Craniofac Surg. May 2008 :659-63.
Randhawa, Premjit S, et al. "Impace of Long-term Nasopharyngeal Airway on Health-Related Quality of Life of Children With Obstructive Sleep Apnea Caused by Syndromic Craniosynostosis" J Craniofac Surg. Jan. 2011, vol. 22, No. 1, pp. 125-128.

* cited by examiner

*Primary Examiner* — Patricia Bianco
*Assistant Examiner* — Tarla Patel
(74) *Attorney, Agent, or Firm* — Venable LLP; Henry J. Daley; Tamatane J. Aga

(57) ABSTRACT

A nasally inserted airway opening device with inflatable cuff is provided to treat obstructive sleep apnea. The airway opening device includes a hollow flexible tube extending between a proximal end and a distal end, and an inflatable cuff attached to the tube at or near the distal end. The inflatable cuff may be inflated and deflated via the tube. The inflatable cuff defines an interior through hole extending along the length thereof. When deflated, the inflatable cuff may be packed closely to the tube and may be inserted or removed through a nostril of a user. When inserted through the user's nostril and positioned in the user's oropharynx or naso-oropharynx and inflated, the inflatable cuff prevents soft tissue in the user's naso-oropharynx from collapsing toward the posterior pharyngeal wall while simultaneously allowing airflow through the through hole. A method for utilizing the airway opening device to prevent/treat sleep apnea is also provided.

15 Claims, 9 Drawing Sheets

NASALLY INSERTED AIRWAY OPENING DEVICE FOR OBSTRUCTIVE SLEEP APNEA TREATMENT

CROSS-REFERENCE TO RELATED APPLICATION

This application claims the priority benefit under 35 U.S.C. §119(e) of U.S. Provisional Application No. 61/412,943, filed Nov. 12, 2010, the entire contents of which are hereby incorporated by reference.

BACKGROUND

1. Field of Invention

The invention relates generally to airway management devices and, more particularly, to a nasally inserted airway opening device with inflatable cuff for obstructive sleep apnea treatment.

2. Discussion of Related Art

Any discussion of the related art throughout the specification should in no way be considered as an admission that such art is widely known or forms part of the general knowledge in the field.

Apnea is a temporary suspension of breathing. Sleep apnea is the temporary cessation of breathing while a person is asleep. Obstructive Sleep Apnea (OSA), a major cause of sleep apnea in adults, results from blockage of the breathing airway to airflow when soft tissue in the oropharynx (e.g., tongue, uvula, etc.) collapses into the posterior pharyngeal wall during sleep.

A number of methods and devices are known for assisting persons afflicted with OSA. Many of these may be self-administered such as, for example, position therapy devices (e.g., pillows, foam wedges), weight loss, avoiding depressants (e.g., alcohol), oral/dental appliances (e.g., mandibular advancement devices), electrostimulation of the airway muscles, and continuous positive airway pressure (CPAP). CPAP, for example, may be self-administered by the afflicted person by switching on a ventilator and applying a mask to the face just prior to sleep. CPAP works by gently blowing pressurized air through the airway at a pressure high enough to keep the airway open and to eliminate apneas that cause hypoxia and resultant awakenings with sleep fragmentation.

Other known methods and devices for assisting persons afflicted with OSA such as, for example, nasal airways and surgical procedures, can be substantially more invasive and typically require the assistance and guidance of qualified medical personnel. Nasal airways, for example, are flexible plastic tubes which are nasally inserted during or shortly after operations to prevent upper airway obstruction in postoperative patients subject to residual anesthetics and/or muscle relaxants. Once inserted, nasal airways are generally well-tolerated by awake patients, but insertion is rather difficult and can be uncomfortable in awake patients due to the tight fit and rubbing of the external tube surface against the nasal airway.

SUMMARY

In an embodiment of the invention, a nasally inserted airway opening device to treat sleep apnea is provided. The airway opening device according to an embodiment of the invention includes a hollow flexible tube extending between a proximal end and a distal end, and an inflatable cuff attached to the tube at or near the distal end. The inflatable cuff may be inflated and deflated via the tube. The inflatable cuff defines an interior through hole extending along the length thereof. When deflated, the inflatable cuff may be packed closely to the tube and may be inserted or removed through a nostril of a user. When inserted through the user's nostril and positioned in the user's oropharynx or naso-oropharynx and inflated, the inflatable cuff prevents soft tissue in the user's oropharynx or naso-oropharynx from collapsing toward the posterior pharyngeal wall while simultaneously allowing airflow through the through hole.

In another embodiment of the invention, a method for utilizing the nasally inserted airway opening device to treat sleep apnea may also be provided. The method according to an embodiment of the invention may include inserting the distal end and deflated cuff of the airway opening device through the user's nostril and nasopharyngeal passageway to a position in the oropharynx or naso-oropharynx. After insertion, the inflatable cuff may be inflated, whereby the inflated cuff prevents soft tissue in the user's oropharynx or naso-oropharynx from contacting the posterior pharyngeal wall while simultaneously allowing airflow through the through hole.

Further features and advantages, as well as the structure and operation of various embodiments of the invention, are described in detail below with reference to the accompanying drawings.

BRIEF DESCRIPTION OF THE DRAWINGS

The foregoing and other features and advantages of the invention will be apparent from the following, more particular description of some embodiments of the invention, as illustrated in the accompanying drawings. Unless otherwise indicated, the accompanying drawing figures are not to scale. Several embodiments of the invention will be described with respect to the following drawings, in which like reference numerals represent like features throughout the figures, and in which.

DETAILED DESCRIPTION

Some embodiments of the invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the invention. All references cited herein are incorporated by reference as if each had been individually incorporated.

Obstructions that cause breathing to stop completely for a predetermined period of time are termed "apneas." When breathing is substantially reduced for a predetermined period of time, it is referred to as a hypopnea. Frequent apneas and hypopneas lead to numerous brief awakenings during sleep and to sleepiness during waking hours. It also significantly contributes to the development of cardiovascular dysfunction such as hypertension and heart hypertrophy. Preventing apneas and hypopneas prevents sleep fragmentation and reduces sleepiness. As used herein, the term "apnea" includes hypopnea.

Figure 1A:
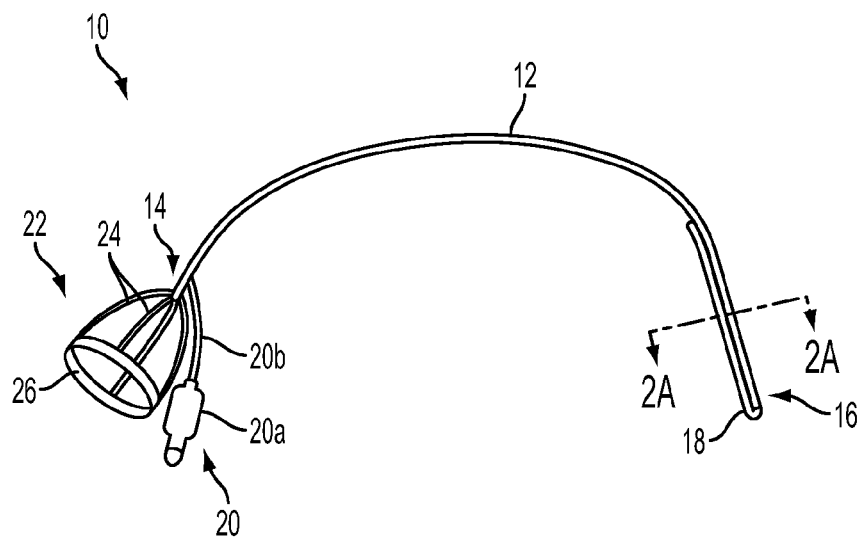
FIG. 1A depicts a perspective view of a nasally insertable airway opening device having an inflatable cuff in a deflated state according to an embodiment of the invention.
Figure 1B:
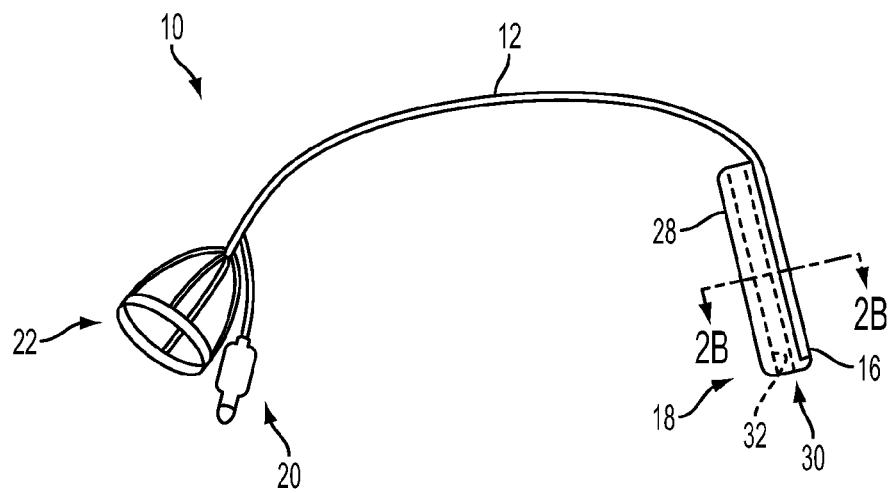
FIG. 1B depicts a perspective view of the nasally insertable airway opening device of FIG. 1A with the inflatable cuff in an inflated state according to an embodiment of the invention.
Figure 2A:
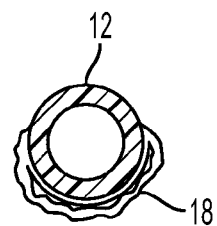
FIG. 2A depicts a cross-sectional view of the airway opening device of FIG. 1A in the deflated state taken along line 2A-2A.
Figure 2B:
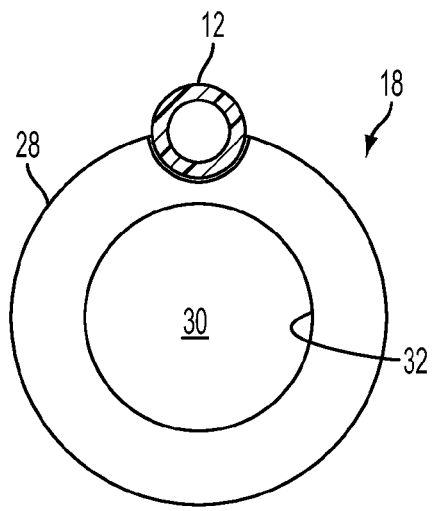
FIGS. 2B-2F depict cross-sectional views of the airway opening device of FIG. 1B in the inflated state taken along line 2B-2B according to a number of possible embodiments.
Figure 2C:
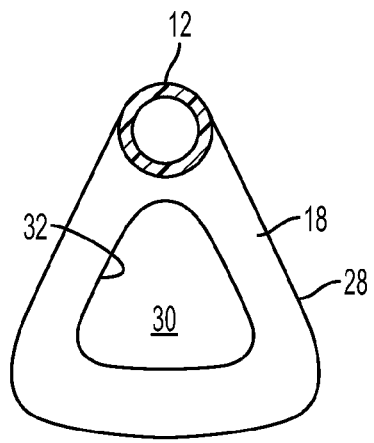
Figure 2D:
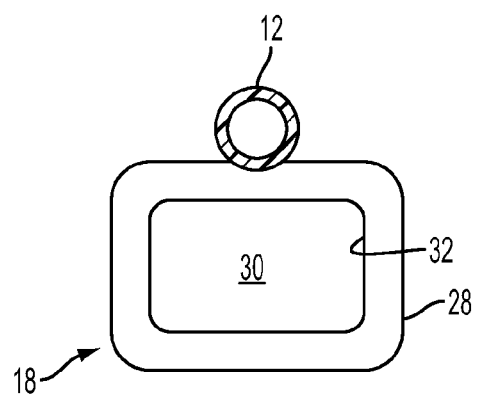
Figure 2E:
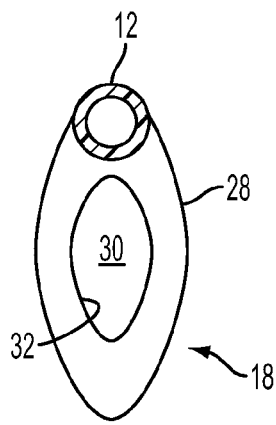
Figure 2F:
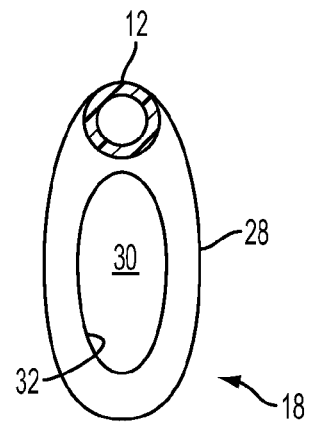

FIGS. 1A and 1B depict perspective views of a nasally insertable airway opening device 10 to treat/prevent sleep apnea according to an embodiment of the invention. The device 10 includes a tube 12 defining a lumen (inflation passage) extending between a proximal end 14 and a distal end 16. An inflatable cuff (balloon) 18 is attached at or near the distal end 16 of the tube 12. A connector 20 may be coupled to or near the proximal end 14 of the tube 12 and may be configured to be coupled to a syringe, plunger, or other inflation mechanism (not shown) for inflation of the cuff 18 via the tube 12. The connector 20 may be self-sealing, for example, by a valve 20a (not shown in further detail), when disconnected from the inflation mechanism, or may include hose clamps (not shown) to crimp a branch tube 20b after inflation of the cuff 18. The tube 12, particularly the distal end 16 with cuff 18 in a deflated state (see FIG. 1A), is configured for insertion through the nostril N and nasopharyngeal passageway (nasal cavity) NP to a position in a user's oropharynx or naso-oropharynx NOP (see FIG. 3). FIG. 2A depicts a cross-sectional view of the airway opening device 10 of FIG. 1A in the deflated state taken along line 2A-2A A nostril blocker member 22 may be coupled at the proximal end 14 of the tube 12. The nostril blocker 22 may be sized and configured to prevent the proximal end 14 of the tube 12 from passing completely through the nostril N and into the nasopharyngeal passageway NP of the user (see FIGS. 3, 4) while still allowing airflow therethrough to allow the user to breathe spontaneously. In this way, nostril blocker 22 can serve dual safety and positioning functions, i.e., preventing the device 10 from being wholly taken into the user's body such as, for example, swallowed, while also ensuring correct placement of the distal end 16 and cuff 18 in the user's oropharynx or naso-oropharynx NOP (see FIG. 3). The nostril blocker 22 may be an open and air-permeable structure such as, for example, a flared or conical member including a plurality of support elements 24 connected at one end to the proximal end 14 of the tube 12 and at another end to a support ring 26. Other forms, shapes and structural features of the nostril blocker 22 are possible and will be apparent to one of ordinary skill in the art.

Figure 2G:
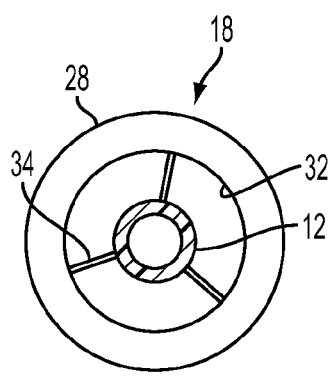
FIG. 2G depicts a cross-sectional view of an airway opening device according to another embodiment.

As shown in the embodiment depicted in FIG. 1B, the cuff 18 may include a through hole 30 extending along a length of the cuff 18. When inflated, the cuff 18 defines an outer surface 28 and an inner surface 32. The outer surface 28 may be configured to contact and mechanically prevent collapse of soft tissues into the posterior pharyngeal wall PW in a user's oropharynx or naso-oropharynx NOP (see FIG. 4). The inner surface 32 may define a structured passageway configured to allow airflow therethrough, enabling the user to breathe spontaneously. FIGS. 2B-2F depict cross-sectional views of the airway opening device 10 of FIG. 1B in the inflated state taken along line 2B-2B according to a number of possible embodiments. The cuff 18 may be coupled to the tube 12, for example, by adhesive or heat welding, although other methods for attachment may also be possible. The cuff 18 may form any number of shapes when inflated such as, for example but not limited to, circular (see FIG. 2B), triangular (see FIG. 2C), rectangular (see FIG. 2D), elliptical (see FIG. 2E), oval (see FIG. 2F), multi-sided, or some combination of these. The inner and outer surfaces 32, 28 may or may not have the same cross-sectional shape. The orientation and attachment point of the cuff 18 may also vary as will be apparent to one of ordinary skill in the art. For example, for oval or elliptical cuffs (FIGS. 2E, 2F), the major and minor axes may be rotated by 90 degrees. For example, for a triangular cuff (FIG. 2C), the attachment point to the tube 12 may be at an apex or along a side thereof. Furthermore, as shown in the embodiment depicted in FIG. 2G, the tube 12 may extend through a center of the through hole 30 and may be connected to the inner surface 32 via one or more spokes 34, through which inflation air may or may not flow to inflate/deflate the cuff 18. The chosen shape and design of the cuff 18 may depend, for example, on maximizing comfort and fit for a particular user based on size/contours of the oropharynx and the position/features of the specific soft tissues targeted for preventing collapse during sleep.

Figure 3:
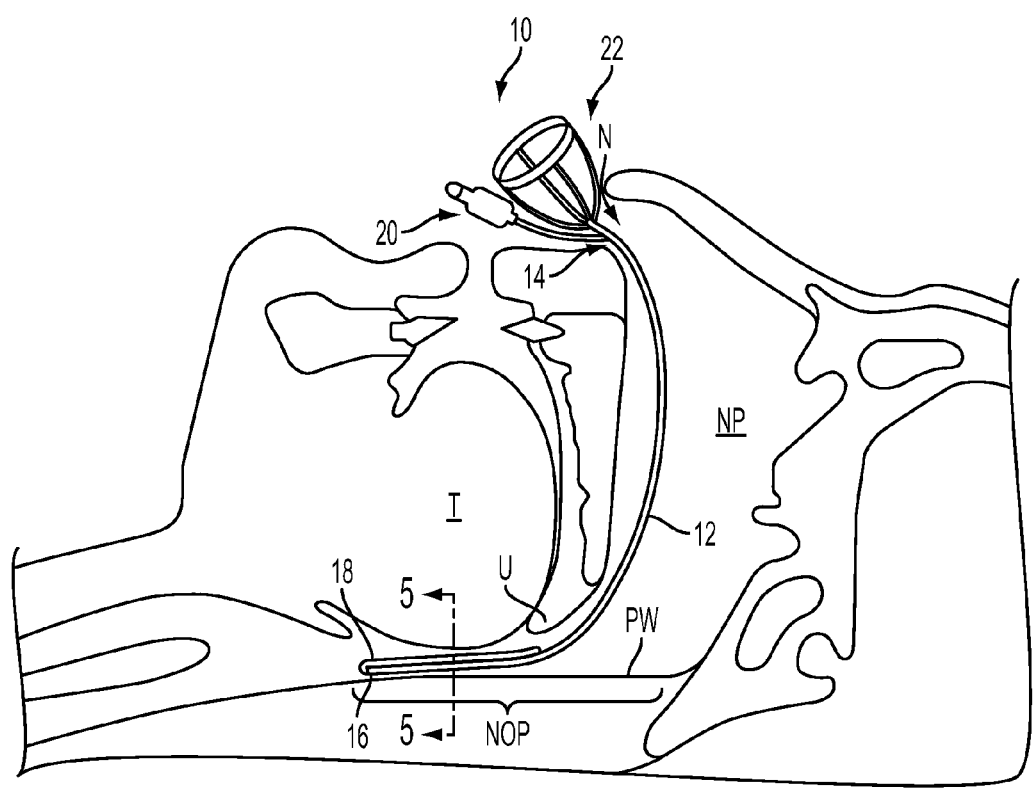
FIG. 3 depicts a side view of the airway opening device of FIG. 1A with the cuff deflated and after insertion through the nostril and nasal cavity of a user according to an embodiment of the invention.
Figure 5:
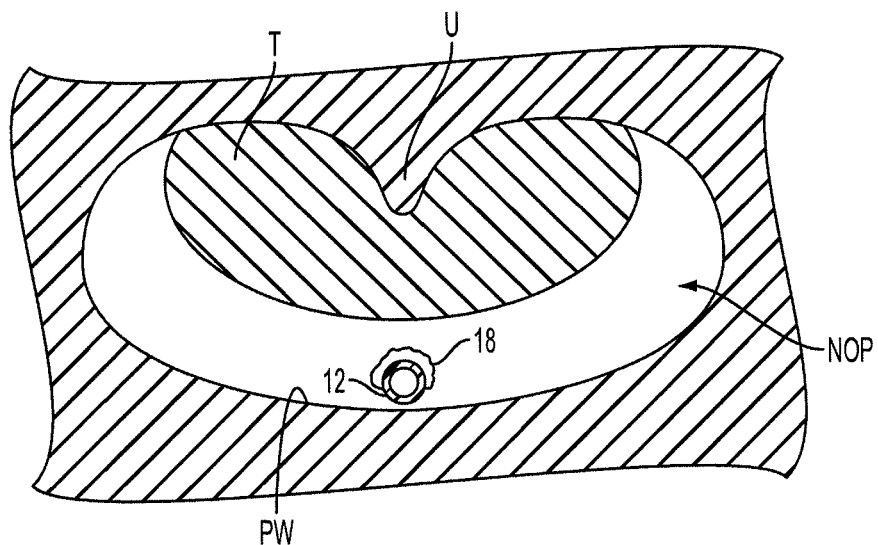
FIGS. 5 and 6 depict cross-sectional views of the airway opening device of FIGS. 3 and 4 in the user's naso-oropharynx and taken along lines 5-5 and 6-6, respectively.

FIG. 3 depicts a side view of the airway opening device 10 of FIG. 1A with the cuff 18 in the deflated state and after insertion through the nostril N and nasal cavity NP of a user according to an embodiment of the invention. When fully inserted by the user, the cuff 18 and distal end 16 of the tube 12 are positioned in the oropharynx or naso-oropharynx NOP just behind the tongue T and/or uvula U and proximate the posterior pharyngeal wall PW. FIG. 5 depicts a cross-sectional view of the deflated cuff 18 and tube 12 of the airway opening device 10 of FIG. 3 in the user's naso-oropharynx NOP and taken along lines 5-5. As shown in FIG. 3, the nostril blocker 22 at the proximal end 14 of the tube 12 may be disposed in the nostril N to prevent further insertion of the device 10 while still allowing airflow through the nostril N. The user may then connect a syringe or other inflation mechanism (not shown) to the connector 20 and begin manually inflating the cuff 18.

Figure 4:
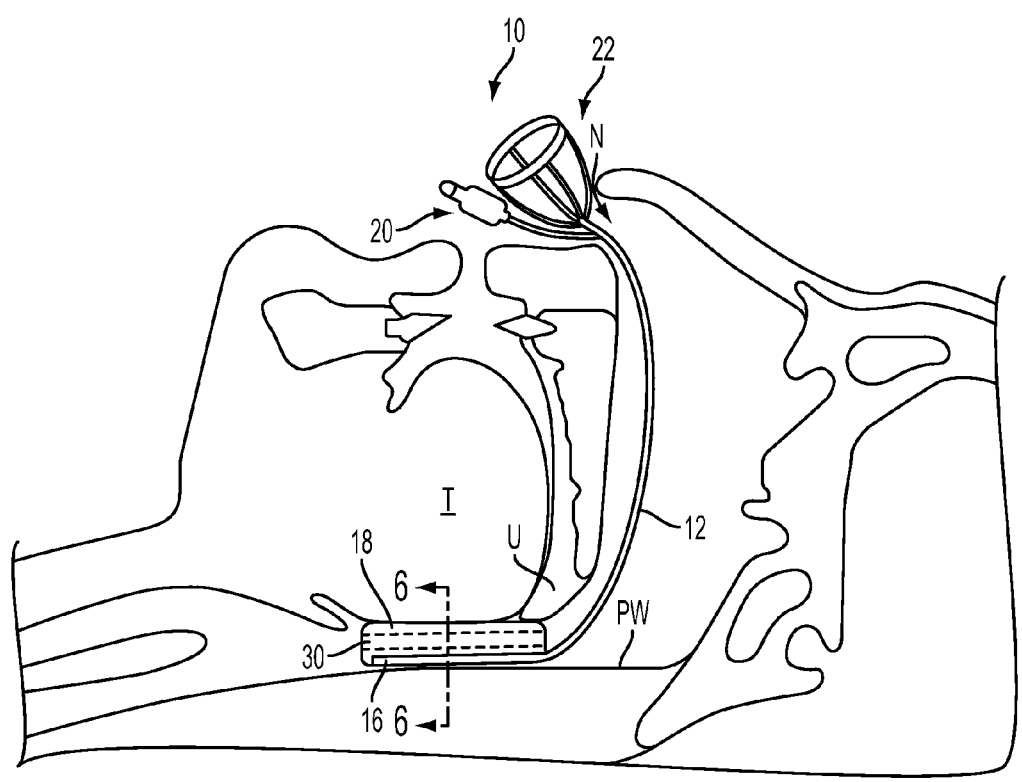
FIG. 4 depicts a side view of the airway opening device of FIG. 1B with the cuff in inflated and positioned in the naso-oropharynx of the user according to an embodiment of the invention.
Figure 6:
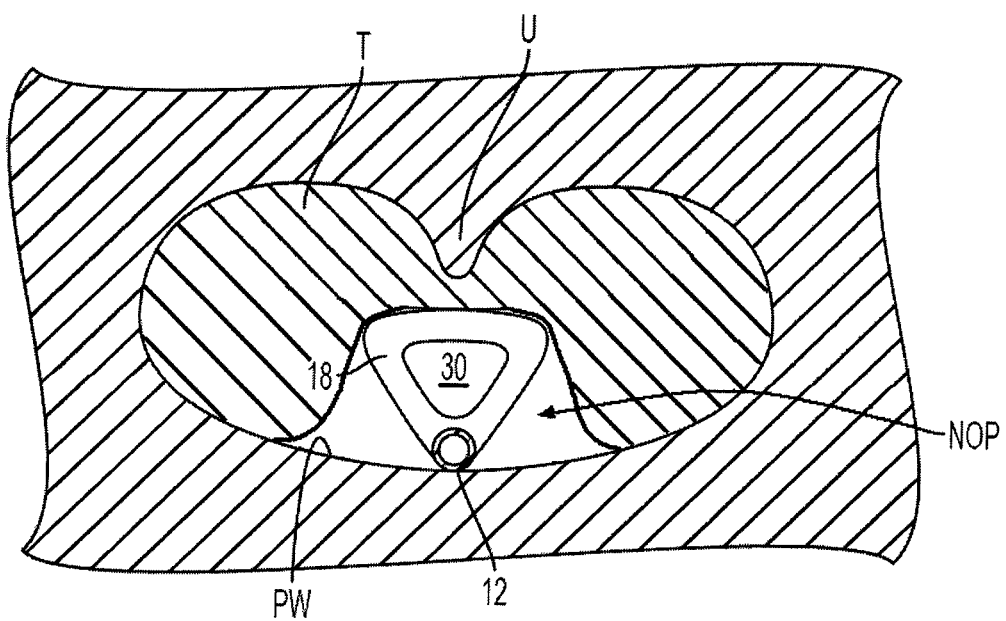

FIG. 4 depicts a side view of the airway opening device 10 of FIG. 1B with the cuff 18 in the inflated state and positioned in the naso-oropharynx NOP of the user. The inflated cuff 18 supports the user's tongue T and/or uvula U and thereby mechanically prevents collapse of these soft tissues into the user's posterior pharyngeal wall PW during sleep. That is, when inflated, cuff 18 pushes the tongue T and/or uvula (soft palate) U away from posterior pharynx PW. The nostril blocker 22 is disposed in the nostril N while still allowing airflow through the nostril N. The through hole 30 maintains a patent airway for airflow during spontaneous breathing of the user even if other unsupported portions of the user's naso-oropharynx collapse toward the posterior pharyngeal wall PW. FIG. 6 depicts a cross-sectional view of the inflated cuff 18 and tube 12 of the airway opening device 10 of FIG. 4 in the user's naso-oropharynx NOP and taken along lines 6-6.

According to an embodiment, the tube 12 may be formed from a variety of suitable materials such as, for example but not limited to, polyvinylchloride (PVC), although other materials are possible so long as they are body tolerated and constructed to provide enough rigidity to prevent collapse, twisting, kinking and/or buckling of the tube during insertion through the nostril N and the nasal cavity NP of the user. The tube 12 may also be flexible enough to avoid causing nasal trauma during insertion and use and may, for example, have a U-shaped curve to ergonomically conform to the nasal cavity NP of the user so that it is easily tolerated and makes atraumatic insertion possible via the nostril N by the user. The tube 12 may have a predetermined length between the proximal and distal ends 14, 16 suitable to extend from the nostril N to the oropharynx of the user. The appropriate length may, for example, be measured and determined by the user's physician or different standard sizes (e.g., length of the tube and length/size of the cuff) may be available and to allow each user to find the most appropriate fit. The tube 12 may also have a small diameter to allow easy insertion through the user's nostril N while minimizing contact with tissues in the nasal cavity NP and naso-oropharynx NOP and having an inner lumen sufficiently sized to allow inflation of the cuff 18 using air or another suitable gas or liquid substance. According to an embodiment, the proximal end 14 of the tube 12 may be closed, such that the branch tube 20b of connector 20 provides the only passageway for the ingress/egress of airflow through the tube 12 (see FIG. 1A). Alternatively, in another embodiment, the proximal end 14 of the tube 12 may be open and the connector 20 may be connected directly thereto (not shown). According to an embodiment, the distal end 16 may be open and fluidly coupled to an interior volume of the cuff 18 such that air flowing through the tube 12 may freely pass in/out of the cuff 18 (see FIGS. 1A, 1B). Alternatively, in another embodiment (not shown), the distal end 16 of the tube 12 may be closed and openings may be provided along an outer radial wall of the tube 12 to fluidly couple the tube lumen to the interior volume of the cuff 18 for inflation/deflation of the cuff 18. According to another embodiment (not shown), the tube 12 may be attached to or integrally formed within a larger airway tube extending from the user's nostril to the oropharynx, which larger airway tube is configured to provide a patent airway throughout the entire nasopharyngeal passageway.

Likewise, the cuff 18 may be formed from a variety of suitable materials such as, for example but not limited to, polyvinylchloride (PVC), although other materials are possible (e.g., polyurethane) so long as they are body tolerated and constructed to provide enough flexibility and durability to withstand multiple inflation/deflation cycles. The cuff 18 should also be soft and flexible enough to avoid causing nasal trauma during insertion and use and suitable for being closely and densely packed about the tube 12 when in the deflated state.

Figure 7:
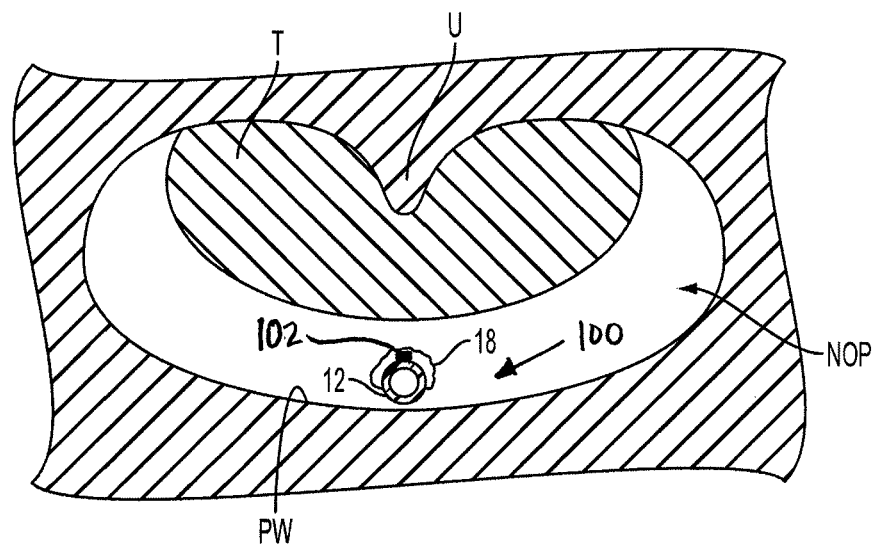
FIGS. 7 and 8 depict a cross-sectional view of an airway opening device including a pressure sensor and positioned in a user's naso-oropharynx according to another embodiment of the invention.
Figure 8:
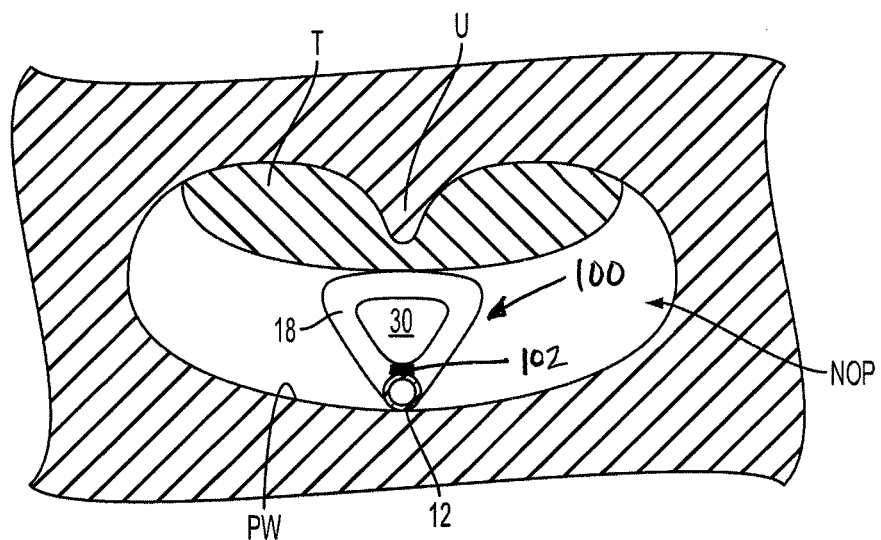

FIGS. 7 and 8 depict a cross-sectional view of an airway opening device 100 in a user's naso-oropharynx NOP according to another embodiment of the invention. The device 100 may be the device 10 of FIGS. 5 and 6 except that it additionally includes a sensor 102. While the inserted device will likely be tolerated by asleep or sedated patients, in some totally awake and/or non-sedated patients inflation of cuff 18 may not be easily tolerated. That is, when the inflated cuff 18 touches the posterior surface of the tongue T it may cause some totally awake and/or non-sedated patients to experience unpleasant sensations or even a gag reflex. Hence, in an embodiment of the invention, the cuff 18 and/or tube 12 may include a sensor 102 configured to sense pressure from the relaxing tongue T and/or uvula U. In this embodiment, the deflated cuff 18 is inserted by the patient prior to sleep and the cuff 18 stays deflated until patient reaches a deep enough level of sleep to start developing an obstruction. If the sensor 102 senses an increasing pressure over a predetermined time period exceeding, for example, twenty or thirty seconds (indicating that the obstruction has developed and hypoxia is imminent), then the sensor 102 may trigger automatic and controlled inflation of the cuff 18. At such time, the patient is likely deeply asleep and should tolerate cuff inflation easily. The sensor 102 may be a known type of pressure sensor such as, for example but not limited to, a pressure transducer (e.g., a strain-gage base transducer) configured to produce an electrical resistance change proportional to the pressure. The sensor 102 may be provided at the level of the cuff 18 such as, for example, on a side of the tube 12 facing the tongue T and uvula U. The sensor 102 may automatically trigger inflation of the cuff 18 by releasing pressurized air which may be stored in the tube 12 itself (e.g., by controlling a valve proximate the cuff—not shown) or by sending a signal to a control device (not shown) coupled to the connector 20 whereby the control device inflates the cuff 18.

Figure 9:
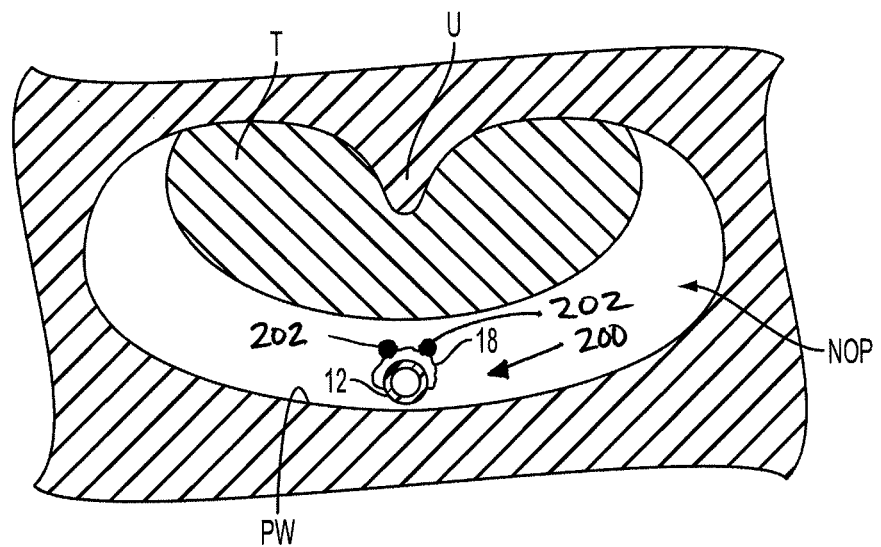
FIGS. 9 and 10 depict a cross-sectional view of an airway opening device including electrical contacts and positioned in a user's naso-oropharynx according to another embodiment of the invention.
Figure 10:
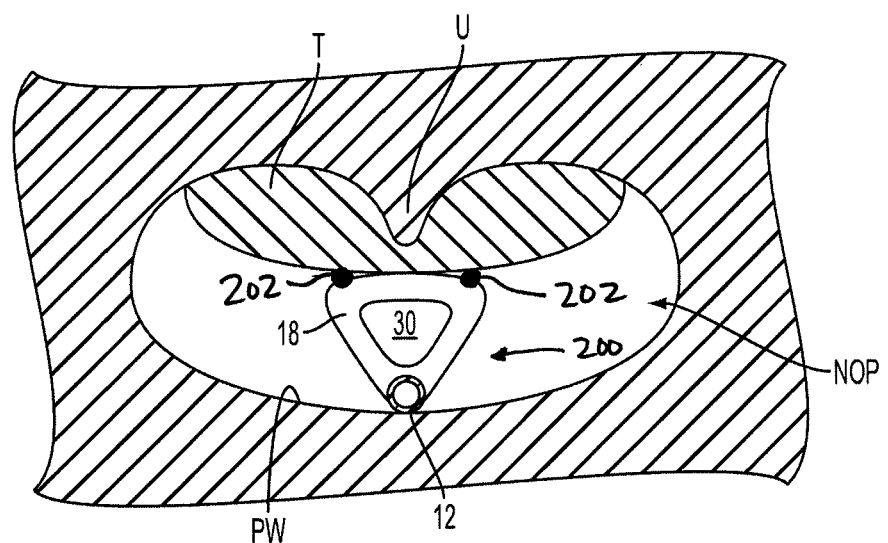
Figure 11:
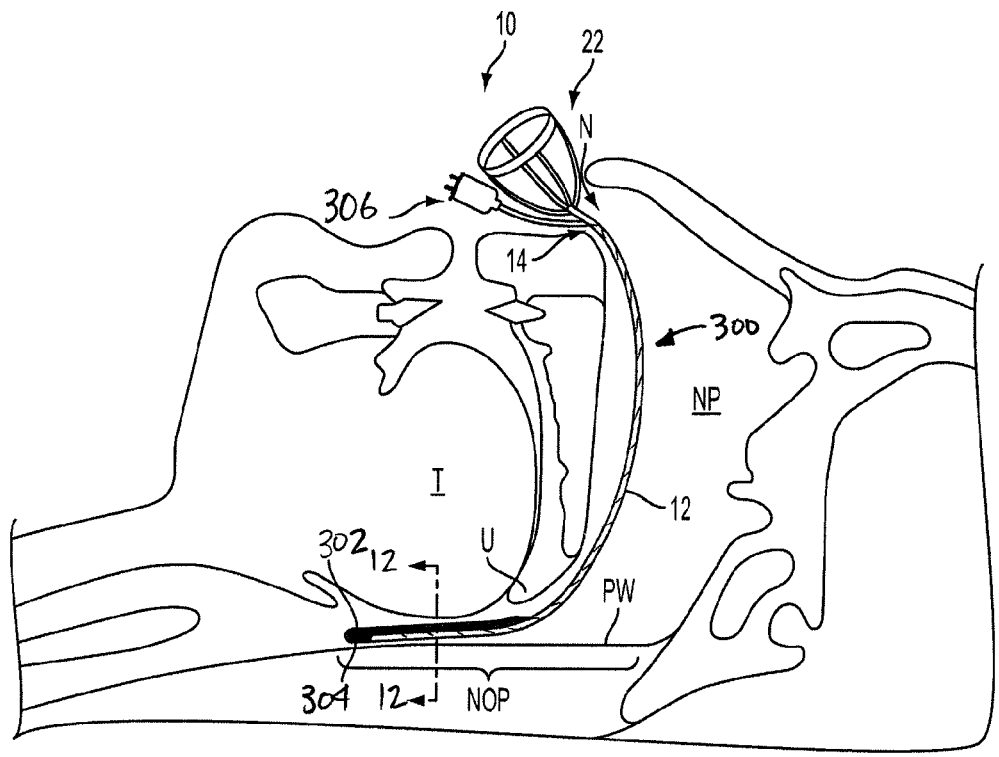
FIG. 11 depicts a side view of an airway opening device according to another embodiment of the invention after insertion through the nostril and nasal cavity of a user.
Figure 12:
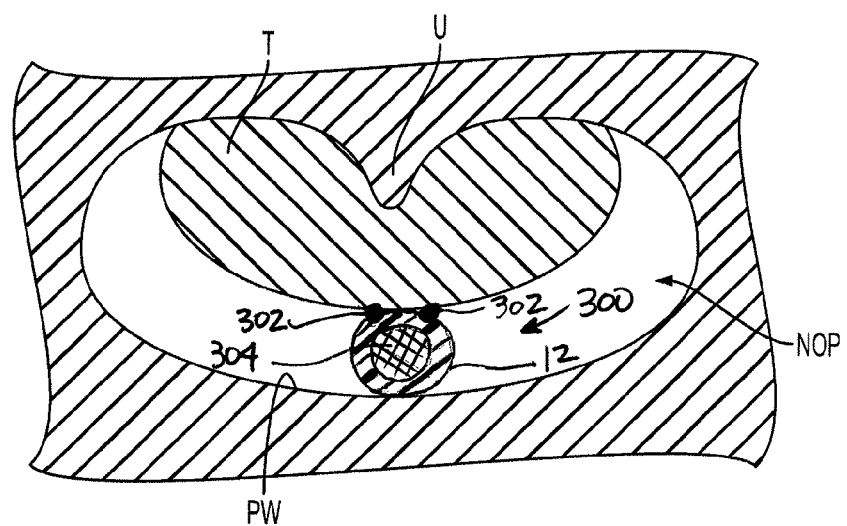
FIG. 12 depicts a cross-sectional view of the airway opening device of FIG. 11 including positioned in a user's naso-oropharynx.

FIGS. 9 and 10 depict a cross-sectional view of an airway opening device 200 in a user's naso-oropharynx NOP according to another embodiment of the invention. The device 200 may be the device 10 of FIGS. 5 and 6 except that it additionally includes electrical contacts 202 such as, for example, two wires or electrical probes, provided at the sides of the cuff 18. When tongue T or other soft tissues collapse on the device 200, they will contact the contacts 202 and close a circuit, thereby serving as an indicator of developing obstruction. This indication may trigger inflation of the cuff 18. Alternatively, or additionally, a small stimulating current might be applied to the contacts 202 to cause muscles in the tongue T or uvula U to contract and move away from the posterior pharyngeal wall PW. Stimulation might be accompanied by cuff inflation, but it is not necessary. For example, as shown in an embodiment depicted in FIGS. 11 and 12, a device 300 may not include an inflatable cuff. Since no cuff inflation is necessary, the device 300 may be tolerated extremely well. The device 300 includes electrical contacts 302 such as, for example, two wires or electrical probes, provided directly on the wall of tube 12. When tongue T or other soft tissues collapse on the device 300, they will contact the contacts 302 and close a circuit, thereby serving as an indicator of developing obstruction. A small stimulating current might be applied to the contacts 302 to cause muscles in the tongue T or uvula U to contract and move away from the posterior pharyngeal wall PW. A small battery 304 such as, for example, a lithium-ion battery, may be provided on or in the device 300, for example, within tube 12 to provide power to the contacts 302. A control device (not shown) such as, for example, a processor may also be provided on or in the device 300, for example, within tube 12. A connector 306 may be provided at the proximal end 14 of the device 300 to allow the battery 304 to be charged between uses.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

I claim:

1. An airway opening device to treat sleep apnea, comprising:
   a hollow flexible tube extending between a proximal end and a distal end; and
   an inflatable cuff attached to the tube at or near the distal end,
   wherein the inflatable cuff is configured to be inflated and deflated via the tube,
   wherein the inflatable cuff defines an interior through hole extending along the length thereof,
   wherein, when deflated, the inflatable cuff is packed closely to the tube and configured to be inserted or removed through a nostril of a user, and
   wherein, when inserted through the user's nostril and positioned in the user's naso-oropharynx and inflated, the inflatable cuff prevents soft tissue in the user's naso-oropharynx from collapsing toward the posterior pharyngeal wall while simultaneously allowing airflow through the through hole,
   wherein, when inflated, a cross-sectional area of the interior through hole of the inflatable cuff is larger than a cross-sectional area of the hollow flexible tube.

2. The airway opening device of claim 1, wherein the inflatable cuff comprises a flexible material, and wherein, when deflated, the inflatable cuff is densely packed along the tube proximate the distal end to facilitate insertion of the distal end of the tube through the user's nostril and nasopharyngeal passageway.

3. The airway opening device of claim 1, further comprising a connector coupled to the proximal end of the tube and configured to be coupled to an inflation mechanism for inflation of the cuff.

4. The airway opening device of claim 3, wherein the proximal end of the tube is closed and the connector includes a branch tube connected near the proximal end.

5. The airway opening device of claim 1, further comprising a nostril blocker attached at the proximal end and configured to prevent passage of the proximal end through the user's nostril.

6. The airway opening device of claim 5, wherein the nostril blocker defines an open and air-permeable flared structure.

7. The airway opening device of claim 5, wherein the nostril blocker includes a plurality of support members coupled to the proximal end of the tube and to a support ring to define a conical structure.

8. The airway opening device of claim 1, wherein the inflatable cuff comprises polyvinylchloride.

9. The airway opening device of claim 1, wherein the tube comprises polyvinylchloride.

10. The airway opening device of claim 1, wherein the tube comprises a curved shape.

11. The airway opening device of claim 1, wherein a cross-section of the inflatable cuff is circular, oval, elliptical, rectangular, triangular, multi-sided, or a combination.

12. The airway opening device of claim 1, further comprising a pressure sensor disposed proximate the distal end of the tube, wherein when the tube is inserted through the user's nostril and positioned in the user's naso-oropharynx, the pressure sensor is configured to detect increasing pressure over a predetermined time period, whereby automatic and controlled inflation of the cuff is triggered.

13. The airway opening device of claim 1, further comprising a plurality of electrical contacts disposed proximate the distal end of the tube, wherein when the tube is inserted through the user's nostril and positioned in the user's naso-oropharynx, soft tissue contacting the electrical contacts closes a circuit, whereby automatic and controlled inflation of the cuff is triggered.

14. The airway opening device of claim 1, further comprising a plurality of electrical contacts disposed proximate the distal end of the tube, wherein when the tube is inserted through the user's nostril and positioned in the user's naso-oropharynx, soft tissue contacting the electrical contacts closes a circuit, whereby a stimulating current is applied through the electrical contacts to the soft tissue.

15. An airway opening device to treat sleep apnea, comprising:
   a hollow flexible tube extending between a proximal end and a distal end;
   a nostril blocker attached at the proximal end and configured to prevent passage of the proximal end through the user's nostril, wherein the nostril blocker includes a plurality of support members coupled to the proximal end of the tube and to a support ring to define a conical structure; and
   an inflatable cuff attached to the tube at or near the distal end,
   wherein the inflatable cuff is configured to be inflated and deflated via the tube,
   wherein the inflatable cuff defines an interior through hole extending along the length thereof,
   wherein, when deflated, the inflatable cuff is packed closely to the tube and configured to be inserted or removed through a nostril of a user, and
   wherein, when inserted through the user's nostril and positioned in the user's naso-oropharynx and inflated, the inflatable cuff prevents soft tissue in the user's naso-oropharynx from collapsing toward the posterior pharyngeal wall while simultaneously allowing airflow through the through hole.

* * * * *